(12) United States Patent
Giles

(10) Patent No.: US 8,628,683 B2
(45) Date of Patent: Jan. 14, 2014

(54) ADDUCT OF 1-HYDROXYETHYLIDENE-1, 1-DIPHOSPHONIC ACID AND ETHYLENEDIAMINE DISUCCINIC ACID OR A SALT THEREOF, A METHOD FOR ITS PREPARATION, AND THE USE OF SAID ADDUCT

(75) Inventor: Matthew Robert Giles, Chester (GB)

(73) Assignee: Innospec Limited (GB)

( * ) Notice: Subject to any disclaimer, the term of this patent is extended or adjusted under 35 U.S.C. 154(b) by 879 days.

(21) Appl. No.: 12/665,123

(22) PCT Filed: Jul. 22, 2008

(86) PCT No.: PCT/GB2008/050612
§ 371 (c)(1),
(2), (4) Date: Jan. 19, 2010

(87) PCT Pub. No.: WO2009/013541
PCT Pub. Date: Jan. 29, 2009

(65) Prior Publication Data
US 2010/0197961 A1    Aug. 5, 2010

(30) Foreign Application Priority Data

Jul. 26, 2007  (GB) .................................. 0714569.1

(51) Int. Cl.
*C09K 3/00*  (2006.01)

(52) U.S. Cl.
USPC ...................................................... 252/182.3

(58) Field of Classification Search
USPC ...................................................... 252/182.3
See application file for complete search history.

(56) References Cited

U.S. PATENT DOCUMENTS 4,704,233 A * 11/1987 Hartman et al. .............. 510/337
2006/0089284 A1   4/2006 Miracle et al.

FOREIGN PATENT DOCUMENTS

| EP | 0713910 | A2 | 10/1995 |
|---|---|---|---|
| EP | 0717102 | A | 6/1996 |
| EP | 1035198 | A2 | 9/2000 |
| GB | 2345065 | A | 6/2000 |
| WO | 9628534 | A | 9/1996 |
| WO | 9702010 | A | 1/1997 |
| WO | 0274273 | A1 | 9/2002 |
| WO | WO 02/074273 | A * | 9/2002 |
| WO | WO 02074273 | A1 * | 9/2002 |
| WO | 0760645 | A3 | 5/2007 |

OTHER PUBLICATIONS

Nowack, B., Chelating agents in the environment, in Biogeochemistry of Chelating Agents; Nowack, B., et al.; ACS Symposium Series; American Chemical Society: Washington, DC, 2005, pp. 1-18.*
PCT International Search Report dated Jan. 23, 2009 for International Appl. No. PCT/GB08/50612.
Search Report under Section 17 dated Nov. 29, 2007 for Great Britain Appl. No. GB 0714569.1.
International Preliminary Report on Patentability and Written Opinion of the International Search Authority, dated Jan. 26, 2010 from parent application PCT/GB2008/050612 filed on Jul. 22, 2008, which claims priority to Great Britain Patent Application No. 0714569.1, filed on Jul. 26 2007.

* cited by examiner

*Primary Examiner* — Johann R Richter
*Assistant Examiner* — Kofi Adzamli
(74) *Attorney, Agent, or Firm* — Burns & Levinson, LLP; Janine M. Susan

(57) ABSTRACT

An adduct of 1-hydroxyethylidene-1,1-diphosphonic acid and from 0.5 to 10 moles of ethylenediamine disuccinic acid or a salt thereof per mole of 1-hydroxyethylidene-1,1-diphosphonic acid, wherein said adduct is in the form of a solid.

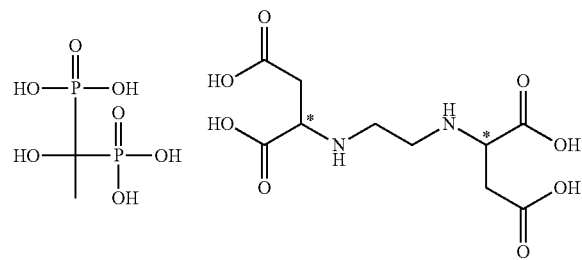

9 Claims, No Drawings

ADDUCT OF 1-HYDROXYETHYLIDENE-1,1-DIPHOSPHONIC ACID AND ETHYLENEDIAMINE DISUCCINIC ACID OR A SALT THEREOF, A METHOD FOR ITS PREPARATION, AND THE USE OF SAID ADDUCT

CROSS-REFERENCE TO RELATED APPLICATIONS

This application is a U.S. national stage application under 35 U.S.C. 371 of co-pending International Application No. PCT/GB08/50612 filed Jul. 22, 2008 and entitled "AN ADDUCT OF 1-HYDROXYETHYLIDENE-1,1-DIPHOSPHONIC ACID AND ETHYLENEDIAMINE DISUCCINIC ACID OR A SALT THEREOF, A METHOD FOR ITS PREPARATION, AND THE USE OF SAID ADDUCT", which in turn claims priority to Great Britain Patent No. 0714569.1 filed Jul. 26, 2007, both of which are incorporated by reference herein in their entirety for all purposes.

The present invention relates to compositions comprising chelating agents, in particular compositions comprising a mixture of chelating agents. It also relates to methods of preparing such compositions, and uses thereof.

A well known chelating agent is 1-hydroxyethylidene-1,1-diphosphonic acid (HEDP) which is an effective sequestrant of calcium and magnesium ions. It has the structure shown in FIG. 1:

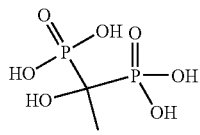

Figure 1

Because it is such an effective sequestrant, HEDP is widely used. For example, it is commonly found in laundry and automatic dishwashing formulations. Commercially available HEDP is sold as a viscous yellow liquid comprising approximately 60 wt % active, and is highly acidic.

Another commonly used chelating agent is ethylenediamine disuccinic acid (EDDS) which has the structure shown in FIG. 2:

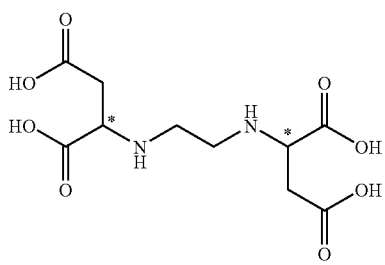

Figure 2

EDDS includes two stereogenic centres and there are three possible stereoisomers. A particularly preferred configuration is [S,S]-ethylenediamine disuccinic acid which is readily biodegradable.

EDDS is an effective chelating agent of transition metals and heavy metals. Transition metals may cause particular problems in compositions containing bleaching agents as they can cause decomposition of peroxygen species. This may result in reduced bleaching performance and the creation of hydroxyl radicals which can cause fibre damage and reduced product stability. Thus it is common to add EDDS to compositions which include a bleaching agent, for example laundry detergent or automatic dishwashing compositions.

In this specification the abbreviation "EDDS" is used to denote the structure shown in FIG. 2 and the same structure in which a number of the hydrogen atoms have been replaced. Thus EDDS may also be used to refer to succinate salts in which 1, 2, 3 or 4 of the acid groups have been neutralised or partially neutralised.

One commercially available material is trisodium ethylenediamine disuccinate. Although this compound can be prepared as a solid, the solid form is very hygroscopic and rapidly absorbs water. The commercial product is therefore supplied as an aqueous solution comprising 30% by weight EDDS (expressed as free acid), or 37 wt % of the trisodium salt (including the counterion).

Another commercially available form of EDDS is the tetra acid. This is provided as a powder which contains 65 wt % solid [S,S] EDDS as an acid and water of crystallisation.

However, each of the above mentioned commercially available materials presents problems for formulators. The tetra acid can readily be incorporated into granular compositions as it is available as a solid but has a solubility in water of just 0.3 g/Kg limiting its suitability for use in laundry and dishwashing applications. The trisodium salt is supplied as a liquid and thus can be difficult to measure and handle and is difficult to incorporate into solid products.

Many consumers are keen to use automatic dishwashing or laundry formulations in the form of a powder or compressed powder tablet but there are no commercially available products which enable readily water soluble solid forms of EDDS to be incorporated directly into laundry or dishwashing compositions.

At present formulators wishing to take advantage of the properties of HEDP and EDDS in formulations must handle two separate products usually supplied as liquids and incur high cost and energy penalties in removing water.

The inventors have found a free flowing solid composition comprising EDDS and HEDP which is readily water soluble and can be easily granulated.

According to a first aspect of the present invention there is a provided an adduct of 1-hydroxyethylidene-1,1-diphosphonic acid and from 0.5 to 10 moles of ethylenediamine disuccinic acid or a salt thereof per mole of 1-hydroxyethylidene-1,1-diphosphonic acid, wherein said adduct is in the form of a solid.

Preferably the adduct is in the form of a free flowing particulate material.

Preferably the adduct may be easily incorporated into a granular composition.

The EDDS component of the adduct may be provided in any suitable form. Preferably it is provided in a form which is water soluble. Preferably the EDDS is present as a metal salt, preferably as a salt of an alkali metal or alkaline earth metal. Most preferably it is present as a sodium salt.

Preferably the EDDS is present in the form of a sodium salt comprising from 1 to 4 moles of sodium, more preferably from 2.5 to 3.5 moles of sodium per mole of EDDS.

Most preferably it is present as a compound having the empirical formula of trisodium ethylenediamine disuccinate.

The adduct of the first aspect of the present invention is preferably the reaction product of trisodium EDDS and HEDP. The exact structure of the adduct is not known but it is thought to be a salt or other coordination complex.

Preferably the adduct comprises at least 0.7 moles of EDDS or a salt thereof per mole of HEDP, more preferably at least 0.9 moles.

The adduct may suitably comprise up to 9 moles of EDDS or a salt thereof per mole of HEDP, for example up to 8 moles, preferably up to 7 moles, preferably up to 6 moles, more preferably up to 5, for example up to 4.5 moles, preferably up to 4, and most preferably up to 3.5 moles of EDDS per mole of HEDP.

The EDDS portion of the adduct of the present invention may include any of the steroisomers. Thus it may be selected from [R,R]-EDDS, [R,S]-EDDS, [S,S]-EDDS and any combination thereof.

Preferably the EDDS is present in substantially the [S,S]-form. Preferably at least 70%, more preferably at least 90% of the EDDS is of the [S,S] configuration.

Preferably the adduct of the present invention is not hygroscopic under normal atmospheric conditions. Preferably it absorbs less than 10% of its weight of water upon exposure to standard atmospheric conditions for 96 hours, preferably less than 8% of its weight, preferably less than 5% of its weight, more preferably less than 3%, preferably less than 2%, and most preferably less than 1.5% of its weight. Preferably it absorbs less than 10% of its weight of water after exposure to atmospheric conditions for 7 days, preferably less than 8%, more preferably less than 7%, preferably less than 5%, most preferably less than 4% of its weight.

The adduct of the present invention preferably has a water solubility of at least 10 g/Kg in water at room temperature, preferably at least 50 g/Kg, more preferably at least 100 g/Kg, more preferably at least 150 g/Kg, preferably at least 175 g/Kg, and most preferably at least 200 g/Kg.

The adduct may have a solubility of up to 600 g/Kg, preferably up to 500 g/Kg, more preferably up to 400 g/Kg and most preferably up to 350 g/Kg.

The above solubility values refer to the weight of succinate present in aqueous solution expressed as the weight of equivalent ethylene diamine disuccinic acid.

According to a second aspect of the present invention, there is provided a composition comprising an adduct of the first aspect.

The composition may consist essentially of the adduct of the first aspect or it may include one or more further components. The composition of the second aspect may be a solid composition or a liquid composition. It may be a composition of any type in which EDDS and/or HEDP has previously been used. In preferred embodiments the composition is a laundry detergent composition or an automatic dishwashing composition.

The composition may be in the form of a particulate material, for example a free flowing powder. Alternatively the composition may be in the form of compressed tablets, or encased, in liquid or solid form, in the shell of water-soluble polymeric material.

The composition may be a granular composition.

Solid laundry compositions of the present invention preferably comprise from 0.01 to 20 wt %, more preferably 0.01 to 4 wt %, most preferably 0.1 to 1 wt % of a salt of the first aspect.

Liquid laundry compositions of the present invention preferably comprise from 0.01 to 50 wt %, more preferably 0.1 to 20 wt %, most preferably 1 to 10 wt % of an adduct of the first aspect.

Automatic dishwashing compositions of the present invention preferably comprise 0.1 to 75 wt % of an adduct of the first aspect, more preferably 1 to 50 wt % and most preferably 2 to 25 wt %.

Laundry and dishwashing compositions of the present invention preferably comprise further ingredients selected from surfactants, builders, bleaches, bleach activators, redeposition additives, dye transfer inhibitors, enzymes, colorants and fragrances.

The provision of a single combined source of HEDP and EDDS in solid form provides a considerable improvement in the formulation possibilities for manufacturers of products containing these materials. This is particularly valuable in the case of laundry and dishwashing compositions. However, other compositions are also within the scope of the present invention. For example, the composition of the second aspect may comprise a bleaching composition, a cleaning composition, an agricultural composition or a personal care composition.

According to a third aspect of the present invention there is provided a method of preparing an adduct of the first aspect.

Preferably the method of the third aspect involves mixing a solution of a salt of EDDS with a solution of HEDP.

Preferably the salt is a sodium salt, more preferably trisodium EDDS.

Preferably the method includes mixing concentrated aqueous solutions of a salt of EDDS and HEDP. Suitably the salt of EDDS is provided as an aqueous solution comprising from 20 to 50 wt %, more preferably 25 to 35 wt % EDDS (expressed as EDDS free acid), and preferably the HEDP is provided as an aqueous solution comprising from 50 to 80 wt %, more preferably 55 to 65 wt % active.

Preferably no further water is added to the reaction mixture in the method of the third aspect.

Preferably in the method of the third aspect a white solid forms upon stirring the solution formed by admixture after 1 to 4 hours, for example after 2 hours.

In the method of the third aspect residual water may be removed using methods known to those skilled in the art, for example heating under reduced pressure.

The present invention further provides the use of an adduct of the first aspect in one of the ways in which known commercial sources of EDDS and/or HEDP have previously been used.

The present invention provides the use of an adduct of the first aspect as a chelating agent. It may be used as a chelating agent for binding transition metals or alkaline earth metals. Preferably the adduct of the first aspect is used as a chelating agent in environments in which transition metals and alkaline earth metals, especially calcium, are found.

The present invention includes the use of an adduct of the first aspect in detergent compositions, for example laundry or automatic dishwashing compositions.

The present invention also includes the use of an adduct of the first aspect in other applications, for example agricultural applications (e.g. slug pellets, herbicides, foliar feeds, nutrient feeds, hydroponics); pulp and paper bleaching (including mechanical bleaching, chemical bleaching, thermochemical bleaching, during both the Q-stage and the P-stage); personal care applications (hair care, creams); cleaning applications (household, institutional and industrial); oil field applications (scale remover); metal cleaning applications (PCB, electroless plating); as a biocide potentiator; in medical applications (anti-poison, metal delivery); and in food applications, for example as a stabiliser or antioxidant.

The adduct of the first aspect also finds considerable utility as an anti scalant agent.

The present invention will now be further described by way of the following non-limited examples.

EXAMPLE 1

The adducts detailed in table 1 were prepared according to the following method.

The appropriate amount of a 37 wt % aqueous solution of trisodium EDDS was mixed with the stated amount of a 60 wt % aqueous solution of HEDP, with stirring.

In each case a white solid had formed after 2 hours. Any residual water was removed under reduced pressure to provide, in each case, a fine white powder.

TABLE 1

Preparation of adducts

| Example | Na$_3$EDDS (as 37 wt % aqueous solution) | | HEDP (as 60 wt % aqueous solution) | | EDDS:HEDP Ratio |
|---|---|---|---|---|---|
| | Mass (g) | Moles | Mass (g) | Moles | |
| A | 185.0 | 0.19 | 64.84 | 0.19 | 1:1 |
| B | 89.66 | 0.09 | 10.31 | 0.03 | 3:1 |
| C | 100.0 | 0.1 | 7.0 | 0.02 | 5:1 |
| D | 100.0 | 0.1 | 3.94 | 0.011 | 9:1 |

EXAMPLE 2

The solubilities in water at room temperature of the HEDP-EDDS adducts were measured and compared to that of the commercially available tetra acid (65% solid of [S,S] EDDS as an acid, and water of crystallisation). Solubilities were determined using the following method.

An excess of solid material was added to 5 ml of water and stirred overnight. The solution was filtered and the filtrate analysed for EDDS content by HPLC. The solubility values given in table 2 refer to the amount of free EDDS or succinate ion present and are expressed as the weight of equivalent ethylene diamine disuccinic acid.

TABLE 2

Solubility of adducts

| Example | EDDS content of a saturated solution solubility (g/kg) |
|---|---|
| EDDS tetra acid | 0.3 |
| A | 279 |
| B | 230 |
| C | 136 |
| D | 188 |

The results in table 2 show that the HEDP-EDDS adducts of the present invention have a vastly superior solubility compared with the tetra acid form of EDDS.

EXAMPLE 3

Samples of the materials were stored at ambient temperatures and the appearance of the samples and the mass thereof were noted over time.

Table 3 shows how the appearance of the material varied over time.

TABLE 3

Appearance of adducts

| | Initial Appearance | Appearance after 24 hr | Appearance after 48 hr | Appearance after 72 hr |
|---|---|---|---|---|
| A | Free flowing powder | Free flowing powder | Free flowing powder | Free flowing powder |
| B | Free flowing powder | Free flowing powder | Free flowing powder | Free flowing powder |
| C | Free flowing powder | Free flowing powder | Free flowing powder | Slightly sticky solid |
| D | Free flowing powder | Free flowing powder | Slightly sticky solid | Slightly sticky solid |
| Na$_3$EDDS | Free flowing powder | Sticky solid (2 h) | Very stick solid | Very sticky solid |

Table 4a shows how samples of HEDP-EDDS increased in mass over time and table 4b shows how a sample of trisodium EDDS increased in mass over time.

TABLE 4a

Increase in mass over time of product

| Compound | % increase in mass after 7 days |
|---|---|
| A | 3.4 |
| B | 2.0 |
| C | 7.0 |
| D | 9.1 |

TABLE 4b

Increase in mass over time of Na$_3$EDDS

| Compound | % increase in mass after 2 h | % increase in mass after 4 h | % increase in mass after 72 h |
|---|---|---|---|
| Na$_3$EDDS•nH$_2$0 | 7.4% | 8.9% | 25% |

The above results show that the adducts of the present invention are much more stable to storage as a solid under ambient conditions than trisodium EDDS.

The invention claimed is:

1. An adduct of 1-hydroxyethylidene-1,1-diphosphonic acid and from 0.5 to 10 moles of ethylenediamine disuccinic acid or a salt thereof per mole of 1-hydroxyethylidene-1,1-diphosphonic acid, wherein said adduct is in the form of a solid.

2. An adduct according to claim 1 wherein the source of ethylenediamine disuccinic acid is a sodium salt thereof.

3. An adduct according to claim 2 wherein the source of ethylenediamine disuccinic acid is trisodium ethylenediamine disuccinate.

4. An adduct according to claim 1 which is not hygroscopic.

5. An adduct according to claim 1 which has a solubility of at least 10 g/Kg.

6. An adduct according to claim 1 which is in the form of a free flowing particulate material.

7. A composition comprising an adduct as claimed in claim 1.

8. A composition as claimed in claim 7 which is a granular composition.

9. A composition as claimed in claim 7 which is a laundry detergent or automatic dishwashing composition.

* * * * *